(12) United States Patent
Kim et al.

(10) Patent No.: US 9,913,590 B2
(45) Date of Patent: Mar. 13, 2018

(54) WORKOUT MANAGEMENT METHOD AND SYSTEM USING A WEARABLE DEVICE

(71) Applicant: SAMSUNG ELECTRONICS CO., LTD., Suwon-si (KR)

(72) Inventors: Sangkyu Kim, Yongin-si (KR); Joonhyung Lee, Yongin-si (KR); Seongho Cho, Gwacheon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 154 days.

(21) Appl. No.: 14/809,388

(22) Filed: Jul. 27, 2015

(65) Prior Publication Data
US 2016/0107029 A1 Apr. 21, 2016

(30) Foreign Application Priority Data

Oct. 15, 2014 (KR) .................. 10-2014-0139067

(51) Int. Cl.
| | | |
|---|---|---|
| A63B 24/00 | (2006.01) | |
| A61B 5/0402 | (2006.01) | |
| A61B 5/00 | (2006.01) | |
| G06F 19/00 | (2018.01) | |
| A61B 5/11 | (2006.01) | |

(52) U.S. Cl.
CPC .......... *A61B 5/0402* (2013.01); *A61B 5/0022* (2013.01); *A61B 5/1113* (2013.01); *A61B 5/1116* (2013.01); *A61B 5/1118* (2013.01); *A61B 5/1123* (2013.01); *A61B 5/486* (2013.01); *A61B 5/681* (2013.01); *A61B 5/6824* (2013.01); *A61B 5/6895* (2013.01); *A61B 5/742* (2013.01); *A61B 5/7405* (2013.01); *G06F 19/3481* (2013.01); *A61B 2503/10* (2013.01); *A61B 2505/09* (2013.01); *A61B 2562/0219* (2013.01);
(Continued)

(58) Field of Classification Search
CPC ..... A61B 5/0402; A61B 5/486; A61B 5/6895; A61B 5/7405; A61B 5/742; A61B 5/0022; A61B 5/1113; A61B 5/1116; A61B 5/1118; A61B 5/1123; A61B 5/681; A61B 5/6824; A61B 2503/10; A61B 2505/09; A61B 2562/0219; A61B 2562/0223; A61B 2562/0257; G06F 19/3481

See application file for complete search history.

(56) References Cited

U.S. PATENT DOCUMENTS

| | | | | |
|---|---|---|---|---|
| 8,702,430 B2 * | 4/2014 | Dibenedetto | ....... | G06F 19/3418 434/247 |
| 8,749,380 B2 | 6/2014 | Vock et al. | | |

(Continued)

FOREIGN PATENT DOCUMENTS

| | | |
|---|---|---|
| KR | 1020040019209 A | 3/2004 |
| KR | 1020070102140 A | 10/2007 |

OTHER PUBLICATIONS

"Bowflex", Press release, Jun. 25, 2014, Total 2 pages.

*Primary Examiner* — Glenn Richman
(74) *Attorney, Agent, or Firm* — Sughrue Mion, PLLC (57) ABSTRACT

A workout management method performed by a wearable device is provided. The workout management method includes receiving a first information about an amount of exercise to be performed by a user, obtaining a second information about a current fitness state of the user, comparing the first information and the second information, and outputting the result of the comparison to the user.

21 Claims, 8 Drawing Sheets

(52) U.S. Cl.
CPC ............... *A61B 2562/0223* (2013.01); *A61B 2562/0257* (2013.01)

(56) References Cited

U.S. PATENT DOCUMENTS

| | | | | |
|---|---|---|---|---|
| 8,911,328 B2* | 12/2014 | Alessandri | ............ | A63B 21/062 482/1 |
| 2005/0124463 A1* | 6/2005 | Yeo | ................... | A61B 5/02427 482/8 |
| 2007/0060446 A1* | 3/2007 | Asukai | ............... | A63B 24/0021 482/8 |
| 2008/0200312 A1* | 8/2008 | Tagliabue | .......... | A63B 24/0084 482/9 |
| 2009/0221403 A1* | 9/2009 | Chan | .................. | A63B 24/0062 482/8 |
| 2009/0233770 A1* | 9/2009 | Vincent | .............. | A63B 24/0021 482/8 |
| 2010/0009810 A1* | 1/2010 | Trzecieski | ......... | A63B 24/0062 482/8 |
| 2010/0075806 A1* | 3/2010 | Montgomery | ..... | A63B 24/0003 482/8 |
| 2010/0210421 A1* | 8/2010 | Case, Jr. | ................ | A63B 24/00 482/8 |
| 2010/0273610 A1* | 10/2010 | Johnson | ............. | A63B 24/0075 482/9 |
| 2010/0331145 A1* | 12/2010 | Lakovic | .................. | G04F 10/00 482/8 |
| 2011/0092337 A1* | 4/2011 | Srinivasan | ......... | A63B 24/0006 482/8 |
| 2012/0015778 A1* | 1/2012 | Lee | .................... | A63B 71/0622 482/8 |
| 2013/0106684 A1 | 5/2013 | Weast et al. | | |
| 2013/0197680 A1 | 8/2013 | Cobbett | | |
| 2015/0141202 A1* | 5/2015 | Ellis | ..................... | A61B 5/1038 482/8 |
| 2015/0238817 A1* | 8/2015 | Watterson | ........... | G06F 19/3481 |
| 2016/0023043 A1* | 1/2016 | Grundy | .............. | A63B 24/0062 482/8 |
| 2016/0030804 A1* | 2/2016 | Mizuochi | ................ | A61B 5/11 482/8 |

* cited by examiner

WORKOUT MANAGEMENT METHOD AND SYSTEM USING A WEARABLE DEVICE

CROSS-REFERENCE TO RELATED APPLICATION

This application claims priority from Korean Patent Application No. 10-2014-0139067, filed on Oct. 15, 2014 in the Korean Intellectual Property Office, the disclosure of which is incorporated herein in its entirety by reference.

BACKGROUND

1. Field

Apparatuses and methods consistent with exemplary embodiments relate to a workout management system using a wearable device.

2. Description of the Related Art

As interest in a healthy lifestyle is increasing, various types of biomedical information detection apparatuses that measure various biomedical signals in a user's daily life are being developed.

Additionally, such biomedical information detection apparatuses are supplied in a form of a wearable device that may be worn by a user and that directly measure a biomedical state of the user. Thus, such biomedical information detection apparatuses are utilized as smart healthcare systems that provide health-related services by working with personal health information databases and that transmit a diagnosis/prescription result to a patient by working with remote medical professionals.

Additionally, many people use fitness machines at a fitness center so as to compensate for lack of exercise in their daily life. Various fitness machines are used to provide an appropriate amount of exercise required for different body parts of a user. In many situations, a user requires consultation from a professional trainer to check whether a necessary amount of exercise has been completed, so as to effectively use the fitness machine.

SUMMARY

Aspects of one or more exemplary embodiments provide methods and apparatuses for a workout management method and system using a wearable device.

Additional aspects will be set forth in part in the description which follows and, in part, will be apparent from the description, or may be learned by practice of exemplary embodiments.

According to an aspect of an exemplary embodiment, a workout management method performed by a wearable device includes receiving a first information about an amount of exercise to be performed by a user, obtaining a second information about a current fitness state of the user, comparing the first information and the second information and outputting the result of the comparison to the user.

According to another exemplary embodiment, the first information comprises at least one of workout intensity, a number of times a workout is to be performed, and an amount of workout time with respect to one or more fitness machines.

According to another exemplary embodiment, the receiving of the first information comprises receiving the first information from the user directly via an input into the wearable device.

According to another exemplary embodiment, the receiving of the first information comprises receiving the first information from an external electronic apparatus via at least one of a wired or a wireless communication.

According to another exemplary embodiment, wherein the obtaining of the second information includes outputting information about an amount of exercise to be performed by the user with respect to a fitness machine near the user, from among the first information and obtaining information about at least one of a workout intensity and an accumulated amount of exercise performed by the user while the user is using the fitness machine.

According to another exemplary embodiment, the outputting information about an amount of exercise to be performed by the user with respect to a fitness machine comprises displaying the information about the amount of exercise to be performed by the user, with respect to the fitness machine near the user, on a display unit included in the wearable device or a display unit included in the fitness machine near the user.

According to another exemplary embodiment, the outputting information about an amount of exercise to be performed by the user with respect to a fitness machine comprises generating a voice message informing the user of the amount of exercise to be performed by the user with respect to the fitness machine near the user.

According to another exemplary embodiment, the obtaining the information comprises receiving the information about at least one of the workout intensity and the accumulated amount of the workout performed by the user via a wireless communication with the fitness machine.

According to another exemplary embodiment, the obtaining the information comprises counting a number of times the workout is repeated by the user using a sensor included in the wearable device.

According to another exemplary embodiment, the sensor is at least one of an acceleration sensor, a gyroscope sensor, and a terrestrial magnetic sensor.

According to another exemplary embodiment, the comparing further includes comparing the second information to the first information with respect to a fitness machine that is being used by the user, and calculating a remaining amount of exercise to be performed by the user with respect to the fitness machine, determining whether a workout with respect to the fitness machine is completed and outputting a guidance, based on whether or not the workout has been completed, to the user.

According to another exemplary embodiment, the outputting the guidance comprises outputting the guidance using at least one of a display unit, a speaker included in the wearable device, and vibration of the wearable device.

According to another exemplary embodiment, the outputting he guidance comprises generating a voice message or a notification sound notifying that the workout with respect to the fitness machine has been completed, when the workout with respect to the fitness machine has been completed.

According to another exemplary embodiment, the outputting the guidance comprises generating a voice message or a notification sound notifying that the workout with respect to the fitness machine has not been completed, when the user stops operation of the fitness machine or goes away from the fitness machine while the workout with respect to the fitness machine has not been completed.

According to another exemplary embodiment, the workout management method further includes generating a voice message for notifying information about a remaining amount of the exercise to be performed by the user with respect to the fitness machine.

According to another exemplary embodiment, the workout management method further includes accumulating and storing the second information with respect to fitness machines used by the user, based on time.

According to another exemplary embodiment, a non-transitory computer-readable recording storage medium having stored thereon a computer program performs the workout management method, described above, when executed by a computer.

A wearable device includes an input/output (I/O) unit configured to provide an interface with a user, a communicator configured to provide a wireless communication function, a memory configured to store at least one program, and a processor configured to control the I/O unit and the communicator and to execute the at least one program stored in the memory, wherein the at least one program comprises instructions for performing the workout management method described above.

According to another exemplary embodiment, the wearable device can be worn on a wrist.

According to another exemplary embodiment, a workout management system including one or more fitness machines having a wireless communication function, and the wearable device, which can be worn by a user who uses the one or more fitness machines.

According to an aspect of an exemplary embodiment, a workout management method performed by a wearable device includes receiving an input regarding an amount of exercise to be performed by a user on a fitness machine, obtaining a second real time information regarding the amount of exercise performed by the user on the fitness machine, comparing the first information and the second information, and outputting the result of the comparison to the user.

BRIEF DESCRIPTION OF THE DRAWINGS

These and/or other aspects will become apparent and more readily appreciated from the following description of the exemplary embodiments, taken in conjunction with the accompanying drawings in which.

DETAILED DESCRIPTION OF EXEMPLARY EMBODIMENTS

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, exemplary embodiments are merely described below, by referring to the figures, to explain aspects. As used herein, the term "and/or" includes any and all combinations of one or more of the associated listed items. Expressions such as "at least one of," when preceding a list of elements, modify the entire list of elements and do not modify the individual elements of the list.

Hereinafter, exemplary embodiments will be described more fully with reference to the accompanying drawings, in which exemplary embodiments are shown. Like or similar reference numerals in the drawings denote like elements, and thus their description will be omitted.

While such terms as "first," "second," etc., may be used to describe various components, such components must not be limited to the above terms. The above terms are used only to distinguish one component from another.

An expression used in the singular encompasses the expression of the plural, unless it has a clearly different meaning in the context.

it is to be understood that the terms such as "including" or "having," etc., are intended to indicate the existence of the features, numbers, steps, actions, components, parts, or combinations thereof disclosed in the specification, and are not intended to preclude the possibility that one or more other features, numbers, steps, actions, components, parts, or combinations thereof may exist or may be added.

Figure 1:
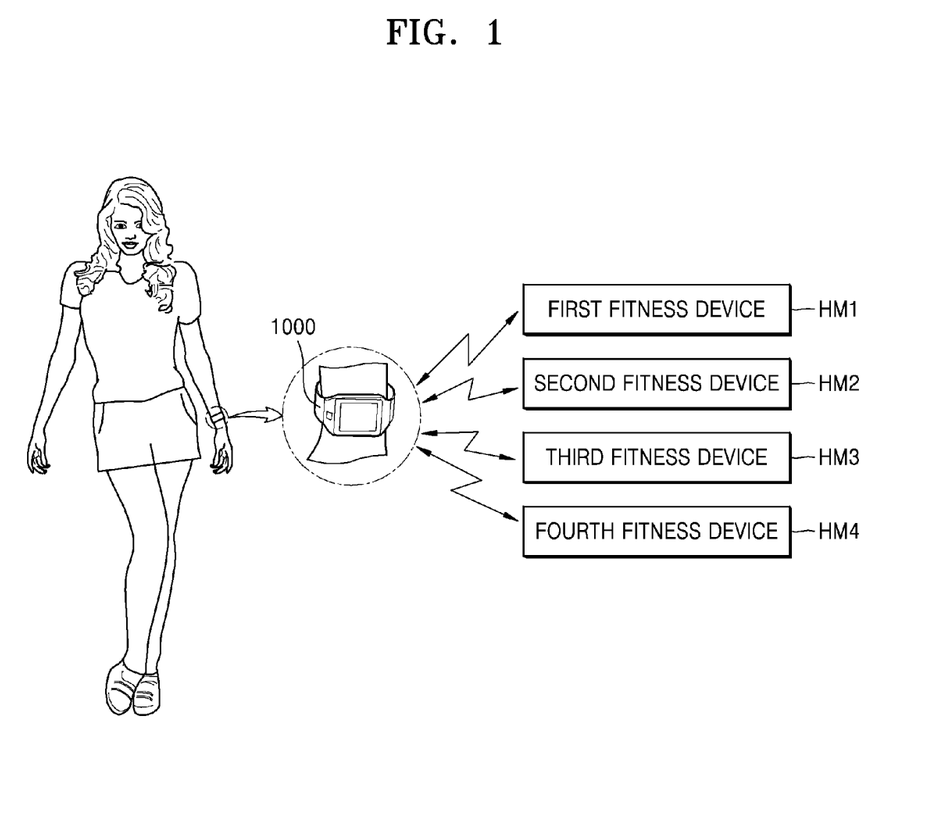
FIG. 1 depicts a schematic block diagram of a workout management system, according to an exemplary embodiment.

FIG. 1 depicts a schematic block diagram of a workout management system, according to an exemplary embodiment.

According to an exemplary embodiment, the workout management system allows a user to manage an amount of exercise by using a wearable device 1000, that may be worn by the user. For this, the workout management system includes at least one fitness machine and the wearable device 1000 that may be worn by a user who uses the at least one fitness machine.

The wearable device 1000 communicates with one of first through four fitness machines HM1 through HM4 which are used by the user, according to an exemplary embodiment, and/or senses a fitness state of the user, and monitors an amount of exercise of the user in real time, based on information regarding a target amount of exercise to be performed by the user. The wearable device 1000 may further provide an appropriate management service to the user.

As shown in FIG. 1, the wearable device 1000 may have a form that may be worn on a wrist, but such a form is not limited thereto.

Figure 2:
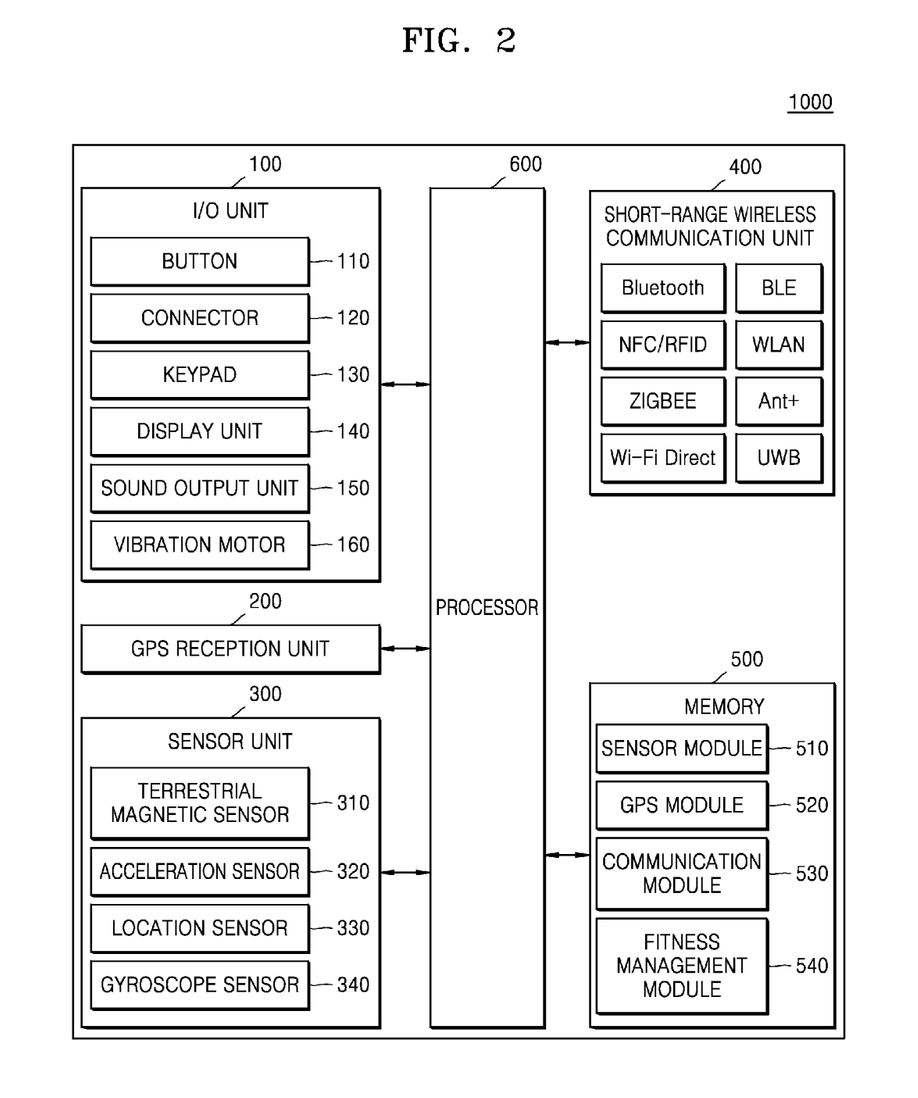
FIG. 2 depicts a schematic block diagram of a wearable device worn by a user, which is included in the workout management system shown in FIG. 1, according to an exemplary embodiment.

FIG. 2 depicts a schematic block diagram of the wearable device 1000 worn by a user, which is included in the workout management system shown in FIG. 1, according to an exemplary embodiment.

In order to perform functions described above, the wearable device 1000 includes an input/output (I/O) unit 100 (e.g., I/O device, inputter/outputter, etc.) for providing an interface with a user, a communication unit 400 (e.g., communicator) for providing a wireless communication function, a memory 500 for storing at least one program, and a processor 600 for controlling the I/O unit 100 and the communication unit 400 and executing a program stored in the memory 500. The wearable device 1000 may further include a sensor unit 300 and a global positioning system (GPS) reception unit 200, according to an exemplary embodiment. A workout/fitness management module 540 that includes commands for performing a workout management service that is to be provided to a user may further be stored in the memory 500.

Hereinafter, elements described above will be described in greater detail.

The I/O unit 100 provides an interface with a user and/or an external device, and may include a button 110, a connector 120, a keypad 130, a display unit 140, a sound output unit 150, and a vibration motor 160, according to an exemplary embodiment.

The I/O unit 100 provides an input unit to which a user may input data for controlling the wearable device 1000. In addition to elements described above, the I/O unit 100 may further include a dome switch or a touch pad that may be a capacitive overlay type, a resistive overlay type, an infrared beam type, a surface acoustic wave type, an integral strain gauge type, or a piezo electric type, but is not limited thereto.

The I/O unit 100 also provides an output unit for outputting an audio signal, a video signal, or a vibration signal. If the display unit 140 and the touch pad form a layered structure to constitute a touch screen, the display unit 140 may be used as an input device as well as an output unit. The display unit 140 may be one of a liquid crystal display (LCD), a thin-film transistor-liquid crystal display (TFT-LCD), an organic light-emitting diode (OLED), a flexible display, a 3-dimensional (3D) display, and an electrophoretic display, but is not limited thereto.

The display unit 140 may output a screen for showing workout management details that are necessary for a user, based on a control by the processor 600. The sound output unit 150 may output a voice message relating to a screen provided as a guide by the display unit 140 based on a control by the processor 600, or output a sound signal such as a notification sound or a warning sound based on a fitness state of the user. The sound output unit 150 may include a speaker or a buzzer, according to an exemplary embodiment. The vibration motor 160 may output a vibration signal. For example, the vibration motor 160 may output a vibration signal together with or instead of the warning sound to indicate an output. Additionally, the vibration motor 160 may output a vibration signal if a touch input is registered on the touchscreen.

The sensor unit 300 may sense a state of the wearable device 1000, such as a motion or location change of the device 1000, and transmit information obtained by the sensing to the processor 600. Thus, the number of times the user wearing the wearable device 1000 repeats exercise, such as the number of times the user performs weight-lifting or abdominal exercise, may be counted.

The sensor unit 300 may include a terrestrial magnetic sensor 310, an acceleration sensor 320, a location sensor 330, and/or a gyroscope sensor 340, according to an exemplary embodiment, but is not limited thereto. Additionally, sensors for detecting a biometric signal such as electrocardiography (ECG), galvanic skin reflex (GSR), or a pulse wave may further be included in the sensor unit 300. Additionally, the sensor unit 330 may also include a temperature/humidity sensor, an infrared sensor, a barometric pressure sensor, or a proximity sensor, but is not limited thereto.

A short-range wireless communication unit 400 provides a function of communicating between the wearable device 1000 and an external device, such as a fitness machine or a smartphone of the user.

The short-range wireless communication unit 400 may include a Bluetooth communication unit, a Bluetooth low energy (BLE) communication unit, a near-field communication unit, a wireless local area network (WLAN) Wi-Fi communication unit, a Zigbee communication unit, an infrared Data Association (IrDA) communication unit, a Wi-Fi Direct (WFD) communication unit, an ultra-wideband (UWB) communication unit, or an Ant+ communication unit, but is not limited thereto.

Although, only the short-range wireless communication unit 400 is shown as an example of a communication unit included in the wearable device 1000, a communication unit included in the wearable device 1000 is not limited thereto, and elements such as a broadcasting receiving unit or a mobile communication unit may further be included in the wearable device 1000.

The memory 500 may store a program for processing and controlling the processor 600. The memory 500 may also store data which is input or output.

The memory 500 may include at least one storage medium selected from the group consisting of a flash memory, a hard disk, a multimedia card micro, a card-type memory such as a secure digital (SD) or extreme digital (XD) memory, a random access memory (RAM), a static random access memory (SRAM), a read-only memory (ROM), an electrically erasable programmable read-only memory (EEPROM), a programmable read-only memory (PROM), a magnetic memory, a magnetic disc, and an optical disc.

Programs stored in the memory 500 may be classified into a plurality of modules according to functions. For example, the programs stored in the memory 500 may be classified into a sensor module 510, a GPS module 520, a communication module 530, and the workout management module 540. Additionally, a user interface (UI) module, a touch-screen module, a notification module, a video playback module, or an audio playback module may further be included based on a function that is to be provided by the wearable device 1000, but the programs are not limited thereto.

The processor 600 generally controls all operations of the device 1000. For example, the processor 600 may execute the programs stored in the memory 500 so as to control the I/O unit 100, the sensor unit 300, and the communication unit 400. Additionally, the processor 600 may provide a workout management service by executing the workout management module 540, so that a user may manage his/her workout when the user exercises using a fitness machine.

Elements of the wearable device 1000 described above are shown as an example of elements required for executing the workout management module 540 stored in the memory 500, which is performed by the processor 600. The workout management module 540 may be included in a wearable device that is implemented in a form of a smart watch having a biomedical signal monitoring function, according to an exemplary embodiment. In this case, an additional element for performing a function of the wearable device 1000, for example, a biomedical authentication module, a biomedical sensor, an analysis module for analyzing a signal received from the biomedical sensor, or the like may further be included in the wearable device.

In the drawings, each unit, that is, the units included in the I/O unit 100, the sensor unit 300, the communication unit 400, and the memory 500 are optional elements. In other words, any combination of one or more of the units described above may be included in the wearable device 1000 and other units not described above may further be included.

Hereinafter, a workout management service provided by the wearable device 1000 will be described in detail.

Figure 3:
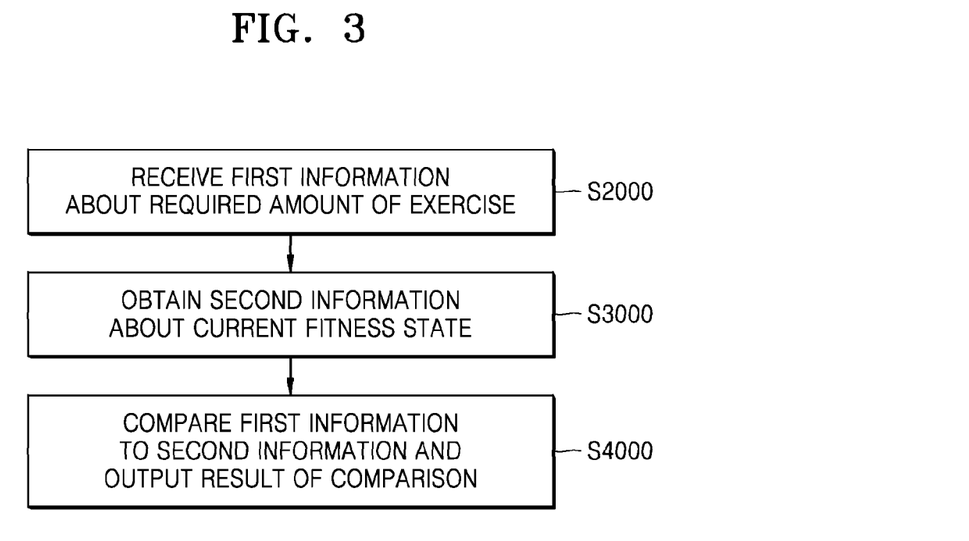
FIG. 3 depicts a flowchart of a workout management method, according to an exemplary embodiment.

FIG. 3 depicts a flowchart of a workout management method according to an exemplary embodiment.

According to an exemplary embodiment, the wearable device 1000 worn by a user performs the workout management method. The workout management method includes receiving first information about an amount of exercise required for a user in operation 52000, obtaining second information about a current fitness state of the user in operation 53000, and comparing the first information to the second information and outputting a result of the comparison in operation S4000.

Figure 4:
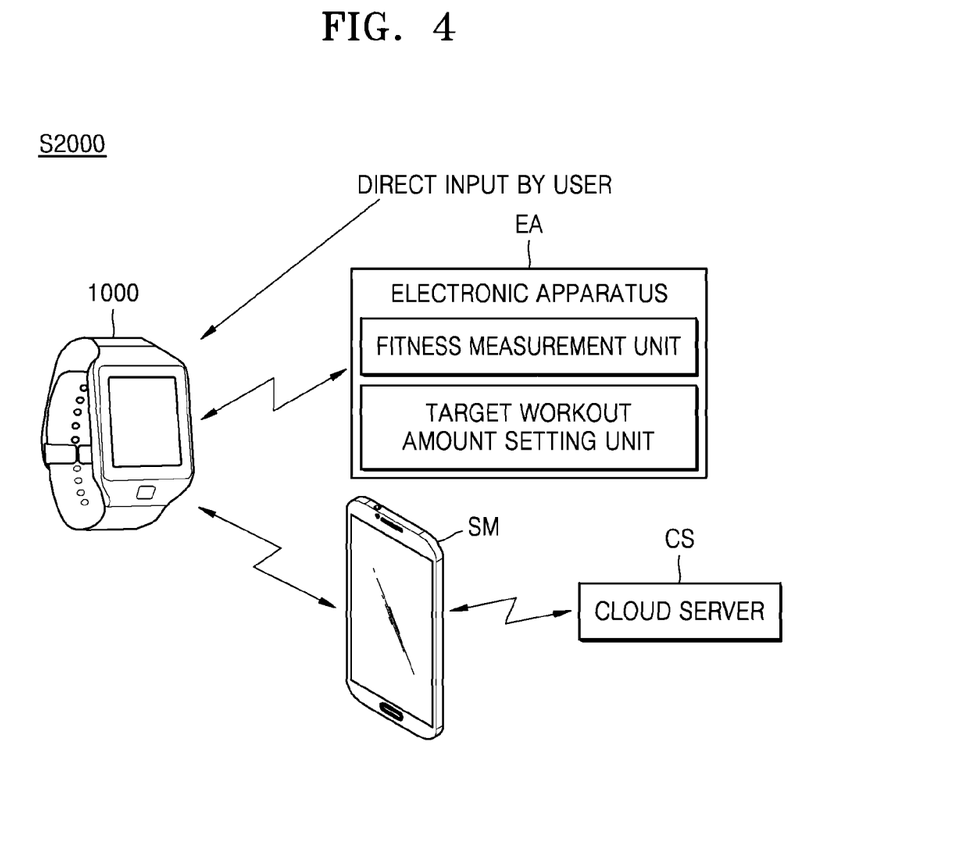
FIG. 4 illustrates an example of a method of receiving first information, which is included in the flowchart shown in FIG. 3, according to an exemplary embodiment.

FIG. 4 illustrates an example of a method of the receiving of the first information, as described in operation 52000 included in the flowchart shown in FIG. 3.

The first information about an amount of exercise required for the user may be information about a target amount of exercise to be performed by the user. The first information may include workout intensity, the number of times a workout routine is performed, or an amount of workout time with respect to one or more fitness machines.

The target amount of exercise to be performed may be arbitrarily set and directly input to the wearable device 1000 by the user via an input unit included in the wearable device 1000.

Alternatively, the target amount of exercise to be performed may be set by a program for measuring physical strength of the user and prescribing appropriate exercise. In many cases, such a service may usually be provided at a fitness center used by the user. In such a scenario, the first information may be received via a wired or wireless communication with an electronic apparatus EA having such a function. The electronic apparatus EA may be configured to include a physical strength/fitness measuring unit and a target workout amount setting unit.

The electronic apparatus EA may not be provided in the fitness center used by the user. In such a scenario, the user may store information about a required amount of exercise, prescribed by the electronic apparatus EA, in another device and input the information to the wearable device 1000, via the other device. Alternatively, the user may store information about a required amount of exercise planned by the user or set by a professional trainer in another device, and input the information to the wearable device 1000, via the other device. For example, the user may transmit information stored in a cloud server CS or another web storage to the wearable device 1000, by using a smartphone SM of the user, as depicted in FIG. 4.

Figure 5:
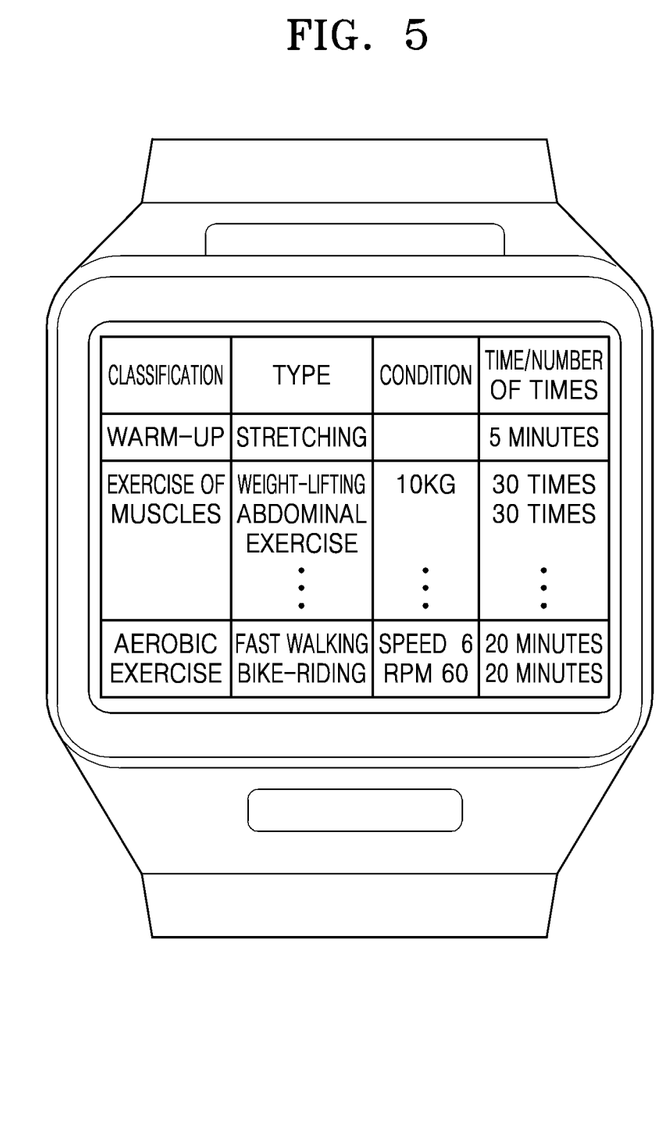
FIG. 5 depicts an example of a screen that is shown on the wearable device according to the receiving of the first information, according to an exemplary embodiment.

FIG. 5 depicts an example of a screen that is shown on the wearable device 1000, according to the receiving of the first information, according to an exemplary embodiment.

The screen depicted in FIG. 5 is only an example, and a target amount of exercise to be performed may be set in a form of calories to be consumed or in a plurality of other form known to one of ordinary skill in the art.

Figure 6:
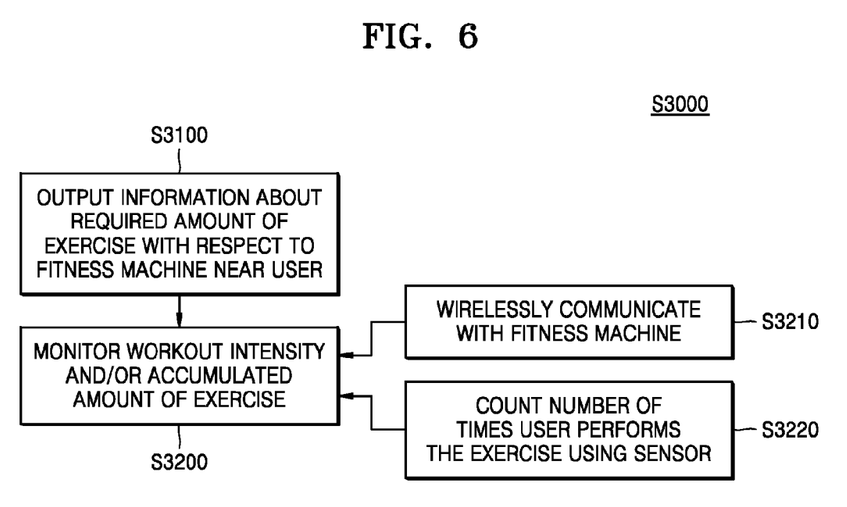
FIG. 6 illustrates an example of a process of obtaining second information, which is included in the flowchart shown in FIG. 3, according to an exemplary embodiment.

FIG. 6 illustrates an example of a process of the obtaining of the second information, included in the flowchart shown in FIG. 3, according to an exemplary embodiment.

The second information is information about a current fitness state of the user, and may include information about a fitness machine that is currently used by the user and an amount of exercise performed by the user, which has been accumulated up to a current point of time.

In operation S3100, the wearable device 1000 may output information about a required amount of exercise with respect to a fitness machine near the user. For example, as shown in FIG. 5, information about the fitness machine near the user may be extracted from information about the target amount of exercise to be performed, and displayed or output as a voice message.

For example, a GPS function provided in the wearable device 1000 may be employed to determine a fitness machine near the user. Location information about fitness machines disposed in the fitness center used by the user may be stored in the wearable device 1000 in advance, and a fitness machine near the user may be determined by comparing the stored location information to the location information of the user in the fitness center which is received from a GPS. Then, information about an amount of exercise required with respect to the fitness machine is extracted from the first information. A result of the extracting may be displayed on the display unit 140 included in the wearable device 1000 and/or output as a voice message. If the fitness machine includes a display unit, information about a target amount of the exercise may be display on the display unit included in the fitness machine.

When the user starts to use the fitness machine according to the guidance provided by the wearable device 1000, the wearable device 1000 monitors a fitness state of the user, that is, the wearable device 1000 monitors the workout intensity and/or accumulated amount of the exercise performed by the user in operation S3200.

To achieve this, the wearable device 1000 may wirelessly communicate with the fitness machine in operation S3210, or a sensor included in the wearable device 1000 may count the number of times the user performs the exercise in operation S3220.

For example, while the user is using a treadmill, the treadmill may provide information about a speed, time, or calories consumed, and the information may be provided to the wearable device 1000 via wireless communication with the wearable device 1000.

When the user exercises using a fitness machine that does not have a wireless communication function, for example, when the user performs weight-lifting or abdominal exercise, an acceleration sensor 320 or the like included in the wearable device 1000 may measure the number of times the user performs weight-lifting or abdominal exercise.

Figure 7:
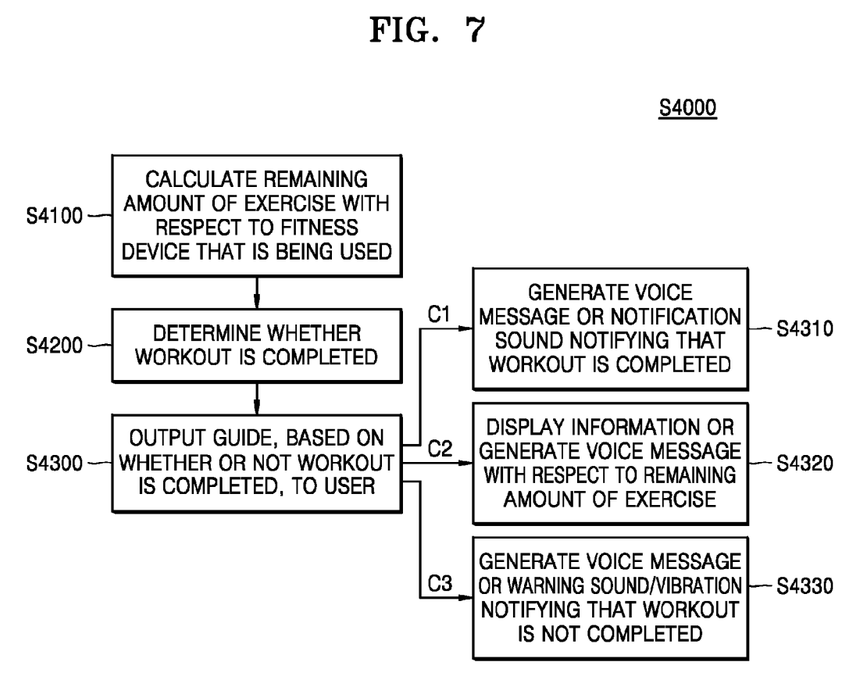
FIG. 7 illustrates an example of a process of a comparison between the first information and the second information and outputting a result of the comparison, which is included in the flowchart shown in FIG. 3, according to an exemplary embodiment.

FIG. 7 illustrates an example of a process of the comparison between the first information and the second information and outputting a result of the comparison in operation S4000, which is included in the flowchart shown in FIG. 3, according to an exemplary embodiment.

The wearable device 1000 calculates a remaining amount of workout with respect to a fitness machine that is being used by a user in operation S4100, and determines whether the workout is completed in operation S4200. Then, in operation S4300, a guide based on whether or not the workout is completed is output to the user.

If the workout is completed (C1), a voice message or a notification sound notifying that the workout is completed is generated in operation S4310. However, such a means of notification is no limited thereto.

When the workout is not completed, while the user is exercising using the fitness machine (C2), information about the remaining amount of the exercise may be displayed or a voice message about the remaining amount of the exercise may be generated in operation S4320. The information about the remaining amount of the exercise is displayed on the display unit 140 included in the wearable device 1000, or on a display unit included in the fitness machine that is being used by the user if the fitness machine includes the display unit. When the information about the remaining amount of the exercise is notified via a voice message, the voice message may be generated at a predetermined point of time, for example, when an achievement rate is 50% or when an achievement rate is 90%. However, such a means of notification is no limited thereto.

When the workout is not completed, if the user stops operation of the fitness machine or goes away from the fitness machine (C3), the wearable device 1000 may generate a voice message, a warning sound, or vibration which notifies that the workout is not completed in operation S4330. However, such a means of notification is no limited thereto. It may be determined whether the operation of the fitness machine is stopped, for example, via a wireless communication with the fitness machine. It may be determined whether the user goes away from the fitness machine, by using the GPS function provided to the wearable device 1000.

FIGS. 8 through 12 illustrate examples that user exercise according to a workout management method, according to an exemplary embodiment.

Figure 8:
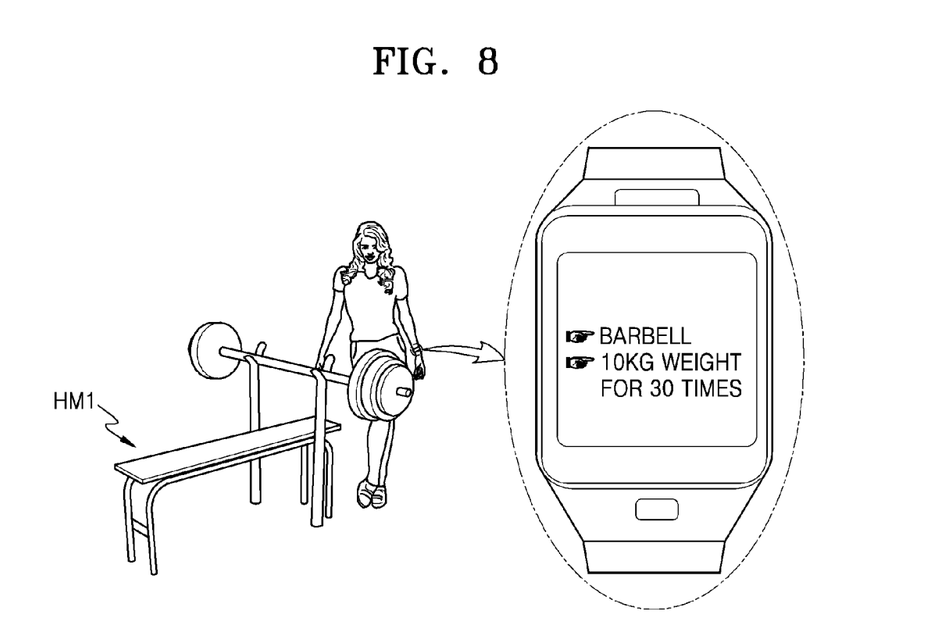
FIGS. 8 through 12 illustrate examples that user exercise according to a workout management method, according to an exemplary embodiment.

Referring to FIG. 8, the user may get close to the first fitness machine HM1 for weight-lifting, for example, according to a guide to the target amount of exercise to be performed as described with reference to FIG. 5. The first fitness machine HM1 may be a barbell. If the wearable device 1000 worn by the user senses that the user is close to the fitness machine HM1, the barbell, the wearable device 1000 extracts information about weight-lifting from stored first information, and displays a target amount of exercise to be performed with respect to the fitness machine HM1 on the display unit 140 included in the wearable device 1000, according to an exemplary embodiment.

Figure 9:
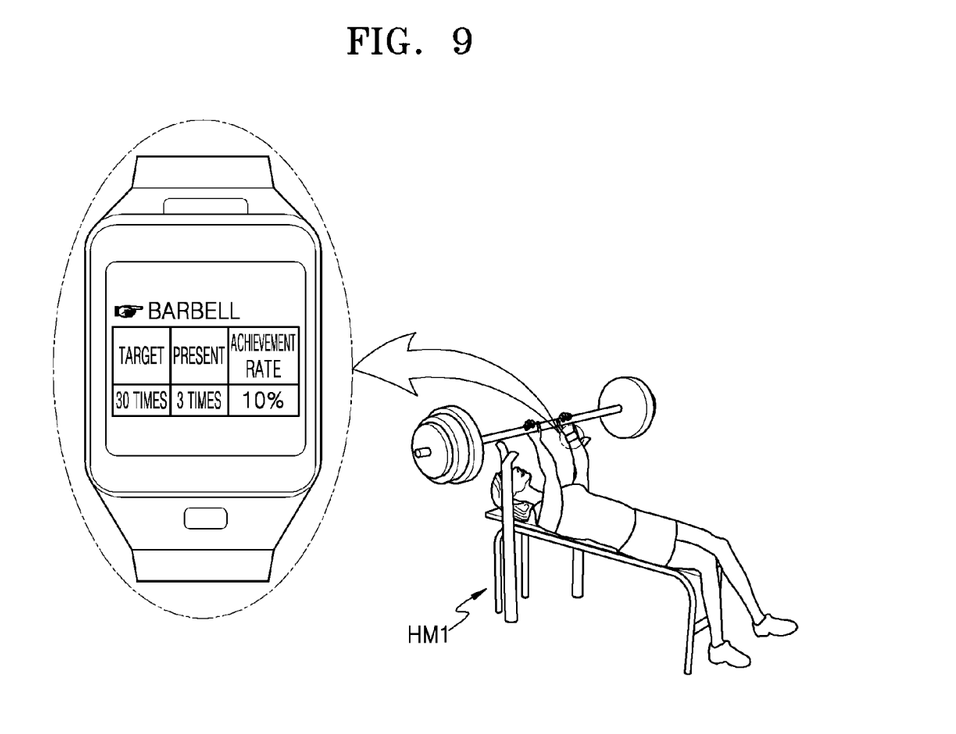

The user starts workout by using the fitness machine MH1 according a guide shown on the displayed unit 140 included the wearable device 1000. While the user is exercising, the wearable device 1000 worn by the user monitors a fitness state of the user. In this case, a sensor included in the wearable device 1000, for example, an acceleration sensor may measure and count the number of times the user has performed weight-lifting. A result of the monitoring may be displayed on the display unit 140 included in the wearable device 1000, according to an exemplary embodiment. Additionally, a guidance message about a remaining amount of the workout or a percentage of workout completed may be provided by the sound output unit 150 included in the wearable device 1000, as shown in FIG. 9. The guidance message about the remaining amount of the workout may be provided once or for a plurality of times at a predetermined point of time.

As a result of the monitoring, if an achievement rate of a target amount of the workout that is to be performed by using the first fitness machine HM1 reaches 100%, the wearable device 1000 may guide the user that the workout to be performed by using the first fitness machine HM1 is completed via a voice message or a notification sound.

Additionally, a fitness machine that is to be used for next workout and a target amount of the next workout may be output on a screen or as voice information, according to an exemplary embodiment.

Figure 10:
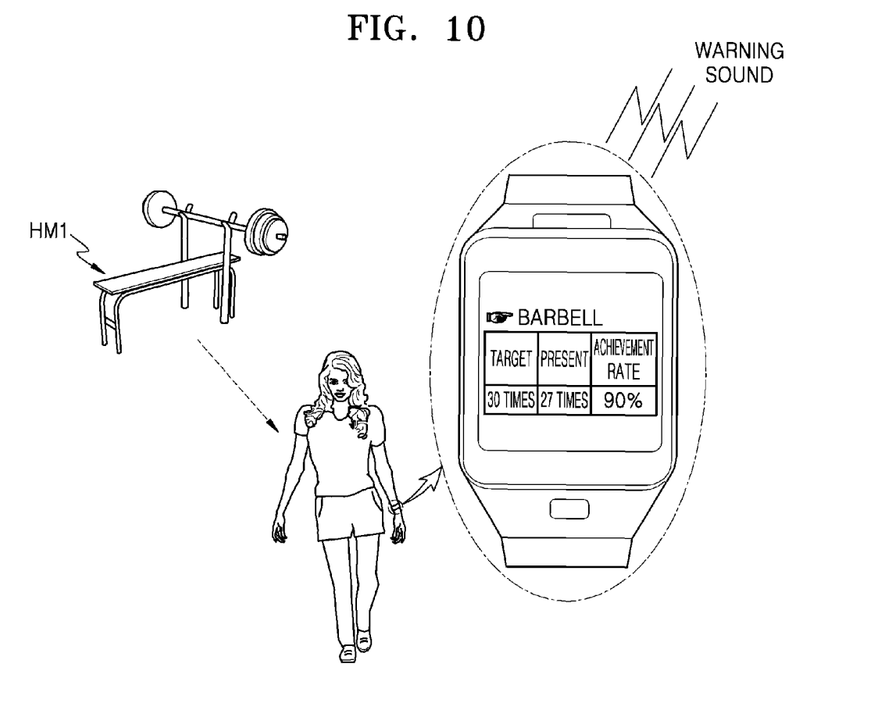

As shown in FIG. 10, when the target amount of exercise to be performed is not completed, if the user goes away from the first fitness machine HM1, the wearable device 1000 may generate a warning sound or vibration or a display message. Alternatively, the wearable device 1000 may generate a voice message notifying that the workout is not completed.

According to the guidance received from the wearable device 1000, the user may return to the first fitness machine HM1 and perform a remaining amount of the workout. The wearable device 1000 may guide the user that the workout to be performed by using the first fitness machine HM1 is completed, and guide a fitness machine to be used to perform next workout and a target amount of the next workout via a screen or voice, according to an exemplary embodiment.

Figure 11:
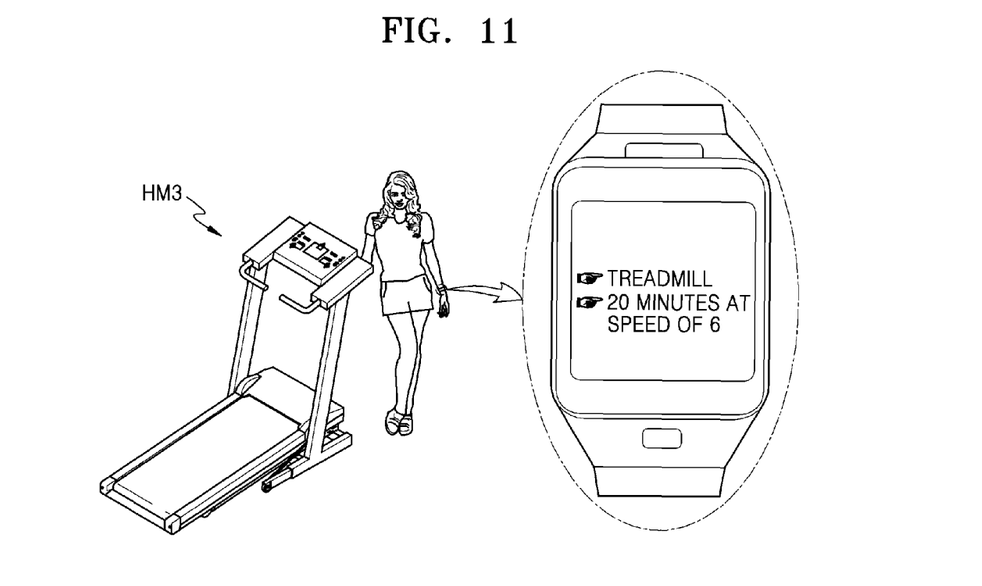

FIG. 11 shows that the user gets close to the third fitness machine HM3, that is a treadmill according to guidance provided by the wearable device 1000. If the user gets close to the fitness machine HM3, the treadmill, the wearable device 1000 may extract information about the fitness machine HM3, the treadmill, from the stored first information, and display the information on the display unit 140 included in the wearable device 1000. The information may be also displayed on a display unit D included in the fitness machine HM3, the treadmill, as well as the display unit 140 included in the wearable device 1000.

Figure 12:
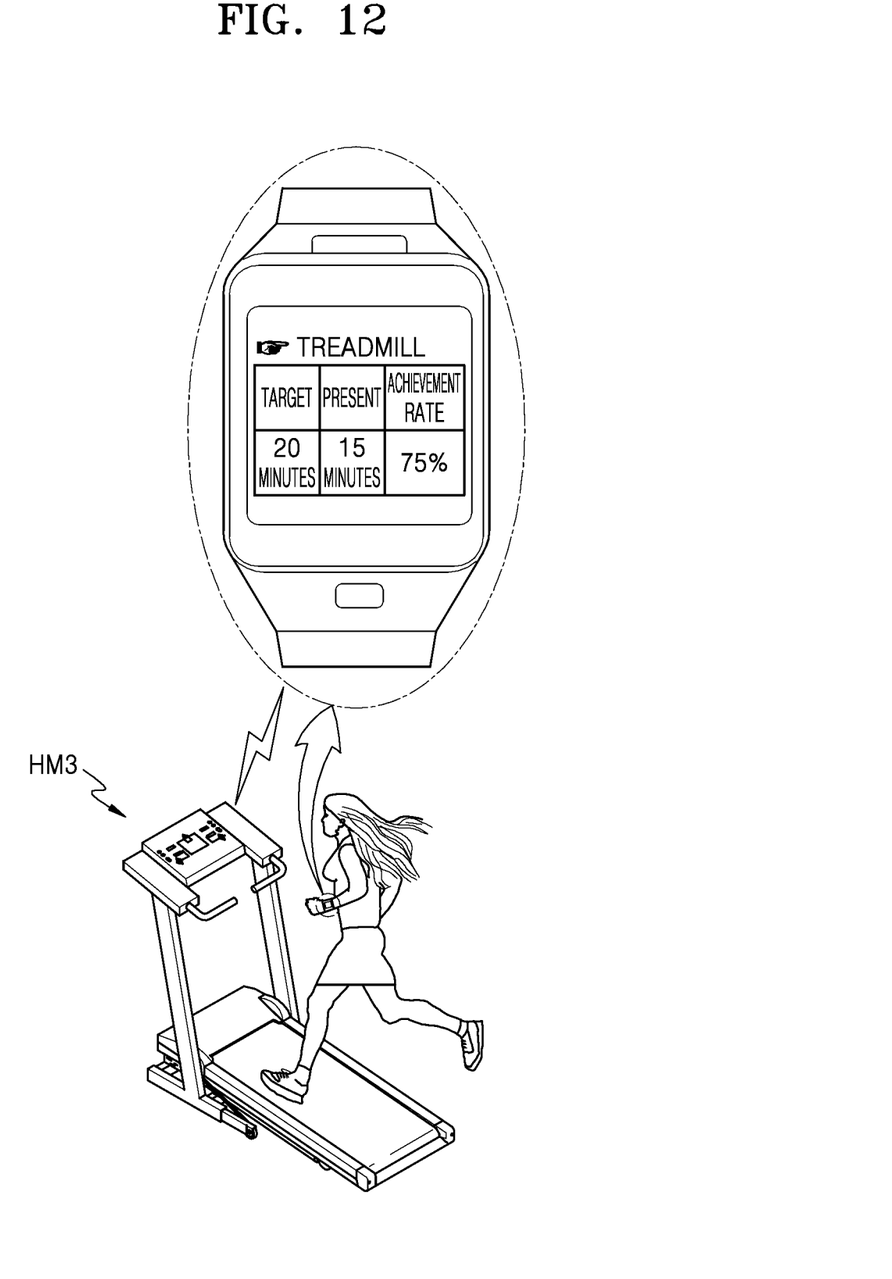

Referring to FIG. 12, while the user is exercising using the fitness machine HM3, the treadmill, information about a state of the user which is measured by the fitness machine HM3, that is, an accumulated amount of the workout such as workout time, consumed calories, or a workout speed is displayed on the display unit 140 included in the wearable device 1000 via communication between the wearable device 1000 and the fitness machine HM3, the treadmill.

Likewise, if a target amount of exercise to be performed is completed, the wearable device 1000 notifies to the user that the workout with respect to the fitness machine HM3 is completed, y receiving the workout information wirelessly from the fitness machine HM3, the treadmill. When the target amount of exercise to be performed is not completed, if operation of the fitness machine HM3, the treadmill is stopped or if the user goes away from the fitness machine HM3, the treadmill, the wearable device 1000 may generate a warning sound to the user, according to an exemplary embodiment.

As such, the user may wear the wearable device 1000, and achieve a necessary amount of exercise according to guidance provided by the wearable device 1000.

Additionally, the wearable device 1000 may accumulate and store an amount of exercise that the user has performed by using various fitness machines. Information regarding the amount of the workout may be stored in the wearable device 1000, a smartphone of the user, or a cloud service interlinked with the smartphone. The stored information may be used to perform analysis for managing physical strength of the user. For example, total calories consumed by performing workout may be analyzed.

As described above, according to one or more of the above exemplary embodiments, the workout management method and system provide a workout management service that allows to easily achieve a target amount of exercise to be performed without having to get help from a personal trainer.

A user may effectively and systematically manage his/her health by wearing a wearable device for performing the workout management method and working out using a fitness machine.

In addition, other exemplary embodiments can also be implemented through computer-readable code/instructions in/on a medium, e.g., a computer-readable medium, to control at least one processing element to implement any above described exemplary embodiment. The medium can correspond to any medium/media permitting the storage and/or transmission of the computer-readable code.

The computer-readable code can be recorded/transferred on a medium in a variety of ways, with examples of the medium including recording media, such as magnetic storage media (e.g., ROM, floppy disks, hard disks, etc.) and optical recording media (e.g., CD-ROMs, or DVDs), and transmission media such as Internet transmission media. Thus, the medium may be such a defined and measurable structure including or carrying a signal or information, such as a device carrying a bitstream according to one or more exemplary embodiments. The media may also be a distributed network, so that the computer-readable code is stored/transferred and executed in a distributed fashion. Furthermore, the processing element could include a processor or a computer processor, and processing elements may be distributed and/or included in a single device.

A "unit" described herein may be a hardware component such as a processor or a circuit, and/or a software component, such as a processor executed by a hardware component.

While the workout management method, and the wearable device and the workout management system used for the workout management method have been particularly shown and described with reference to exemplary embodiments thereof, it will be understood by those of ordinary skill in the art that various changes in form and details may be made therein without departing from the spirit and scope of the exemplary embodiments.

It should be understood that the exemplary embodiments described therein should be considered in a descriptive sense only and not for purposes of limitation. Descriptions of features or aspects within each exemplary embodiment should typically be considered as available for other similar features or aspects in other exemplary embodiments.

While one or more exemplary embodiments have been described with reference to the figures, it will be understood by those of ordinary skill in the art that various changes in form and details may be made therein without departing from the spirit and scope as defined by the following claims.

What is claimed is:

1. A workout management method performed by a wearable device, the workout management method comprising:
   receiving, by the wearable device, a first information about an amount of exercise to be performed by a user;
   obtaining, by the wearable device, a second information about a current fitness state of the user;
   comparing, by the wearable device, the first information and the second information; and
   outputting, by the wearable device, a result of the comparison to the user,
   wherein the obtaining the second information comprises:
   determining, by the wearable device, a fitness machine near the user based on location information related to the wearable device and the fitness machine.

2. The workout management method of claim 1, wherein the first information comprises at least one of workout intensity, a number of times a workout is to be performed, and an amount of workout time with respect to one or more fitness machines.

3. The workout management method of claim 1, wherein the receiving of the first information comprises receiving the first information from the user directly via an input into the wearable device.

4. The workout management method of claim 1, wherein the receiving of the first information comprises receiving the first information from an external electronic apparatus via at least one of a wired or a wireless communication.

5. The workout management method of claim 1, wherein the obtaining of the second information comprises:
   outputting information about an amount of exercise to be performed by the user with respect to the fitness machine near the user, from among the first information; and
   obtaining information about at least one of a workout intensity and an accumulated amount of exercise performed by the user while the user is using the fitness machine.

6. The workout management method of claim 1, wherein the obtaining of the second information comprises: outputting information about an amount exercise to be performed bar the user with respect machine near the user, from among the first information by displaying the information about the amount of exercise to be performed by the user, with respect to the fitness machine near the user, on a display unit included in the wearable device or a display unit included in the fitness machine near the user.

7. The workout management method of claim 1, wherein the obtaining of the second information comprises: outputting information about an amount of exercise to be performed by the user with respect to the fitness machine near the user, from among the first information by generating a voice message informing the user of the amount of exercise to be performed by the user with respect to the fitness machine near the user.

8. The workout management method of claim 1, wherein the obtaining of the second information comprises: obtaining information about at least one of a workout intensity and an accumulated amount of exercise performed by the user while the user is using the fitness machine by receiving the information about at least one of the workout intensity and the accumulated amount of a workout performed by the user via a wireless communication with the fitness machine.

9. The workout management method of claim 1, wherein the obtaining of the second information comprises: obtaining information about at least one of a workout intensity and an accumulated amount of exercise performed by the user while the user is using the fitness machine by counting a number of times the a workout is repeated by the user using a sensor included in the wearable device.

10. The workout management method of claim 9, wherein the sensor is at least one of an acceleration sensor, a gyroscope sensor, and a terrestrial magnetic sensor.

11. A non-transitory computer-readable recording storage medium having stored thereon a computer program which performs the method of claim 1 when executed by a computer.

12. The workout management method of claim 1, wherein the obtaining of the second information comprises:
   obtaining information on an activity performed by the user while the user is using the determined fitness machine.

13. A workout management method performed by a wearable device, the workout management method comprising:
- receiving, by the wearable device, a first information about an amount of exercise to be performed by a user:
- obtaining, by the wearable device. a second information about a current fitness state of the user;
- comparing, by the wearable device, the first information and the second information; and
- outputting, by the wearable device, a result of the comparison to the user,
- wherein the comparing further comprises:
- comparing the second information to the first information with respect to a fitness machine that is being used by the user, and calculating a remaining amount of exercise to be performed by the user with respect to the fitness machine;
- determining whether a workout with respect to the fitness machine is completed; and
- outputting a guidance, based on whether or not the workout has been completed, to the user.

14. The workout management method of claim 13, wherein the outputting the guidance comprises outputting the guidance using at least one of a display unit, a speaker included in the wearable device, and vibration of the wearable device.

15. The workout management method of claim 13, wherein the outputting the guidance comprises generating a voice message or a notification sound notifying that the workout with respect to the fitness machine has been completed, when the workout with respect to the fitness machine has been completed.

16. The workout management method of claim 13, wherein the outputting the guidance comprises generating a voice message or a notification sound notifying that the workout with respect to the fitness machine has not been completed, when the user stops operation of the fitness machine or goes away from the fitness machine while the workout with respect to the fitness machine has not been completed.

17. The workout management method of claim 13, further comprising generating a voice message for notifying information about the remaining amount of the exercise to be performed by the user with respect to the fitness machine.

18. A workout management method performed by a wearable device, the workout management method comprising.
- receiving, by the wearable device, a first information about an amount of exercise to be performed by a user;
- obtaining, by the wearable device. a second information about a current fitness state of the user;
- comparing, by the wearable device, the first information and the second information; and
- outputting, by the wearable device, a result of the comparison to the user; and
- accumulating and storing the second information with respect to fitness machines used by the user, based on time.

19. A wearable device comprising:
- an input/output (I/O) unit configured to provide an interface with a user;
- a communicator configured to provide a wireless communication function;
- a memory configured to store at least one program; and
- a processor configured to control the I/O unit and the communicator and to execute the at least one program stored in the memory,
- wherein the at least one program comprises instructions for performing the method of claim 1.

20. The wearable device of claim 19, wherein the wearable device is configured to be worn on a wrist.

21. A workout management system comprising:
- one or more fitness machines having a wireless communication function; and
- a wearable device configured to be worn by a user who uses the one or more fitness machines, the wearable device comprising:
- an input/output (I/O) unit configured to provide an interface with the user;
- a communicator configured to provide the wireless communication function;
- a memory configured to store at least one program; and
- a processor configured to control the I/O unit and the communicator and to execute the at least one program stored in the memory,
- wherein the at least one one)comprises instructions for performing the method of claim 1.

* * * * *